United States Patent
Agus et al.

(10) Patent No.: US 10,702,176 B2
(45) Date of Patent: Jul. 7, 2020

(54) MULTIELECTRODE ECG SENSOR

(71) Applicants: Children's Medical Center Corporation, Boston, MA (US); Theranova, LLC, San Francisco, CA (US)

(72) Inventors: Michael Agus, Newton, MA (US); Daniel R. Burnett, San Francisco, CA (US); Marcie Lynne Hamilton, San Francisco, CA (US)

(73) Assignees: Children's Medical Center Corporation, Boston, MA (US); Theranova, LLC, San Francisco, CA (US)

( * ) Notice: Subject to any disclaimer, the term of this patent is extended or adjusted under 35 U.S.C. 154(b) by 426 days.

(21) Appl. No.: 15/504,846

(22) PCT Filed: Aug. 21, 2015

(86) PCT No.: PCT/US2015/046279
§ 371 (c)(1),
(2) Date: Feb. 17, 2017

(87) PCT Pub. No.: WO2016/029106
PCT Pub. Date: Feb. 25, 2016

(65) Prior Publication Data
US 2017/0273591 A1 Sep. 28, 2017

Related U.S. Application Data

(60) Provisional application No. 62/040,766, filed on Aug. 22, 2014.

(51) Int. Cl.
*A61B 5/0408* (2006.01)
*A61B 5/00* (2006.01)

(52) U.S. Cl.
CPC ........ *A61B 5/04085* (2013.01); *A61B 5/0408* (2013.01); *A61B 5/6823* (2013.01); *A61B 5/6832* (2013.01); *A61B 2503/04* (2013.01); *A61B 2562/0209* (2013.01); *A61B 2562/043* (2013.01); *A61B 2562/222* (2013.01); *A61B 2562/227* (2013.01)

(58) Field of Classification Search
CPC .................................................. A61B 5/04085
See application file for complete search history.

(56) References Cited

U.S. PATENT DOCUMENTS 4,121,575 A * 10/1978 Mills .................. A61B 5/04085
600/382
5,042,481 A 8/1991 Suzuki et al.
(Continued)

OTHER PUBLICATIONS

International Search Report and Written Opinion for Application No. PCT/US2015/046279 dated Nov. 9, 2015.

*Primary Examiner* — Lee S Cohen
(74) *Attorney, Agent, or Firm* — Wolf, Greenfield & Sacks, P.C.

(57) ABSTRACT

A multielectrode sensor for use in obtaining electrocardiograph measurements of a patient is disclosed. The sensor includes a substrate, at least a portion of the substrate being stretchable, and a plurality of electrodes coupled to the substrate. A distance between at least two of the electrodes is adjustable by stretching the substrate between the at least two electrodes.

26 Claims, 6 Drawing Sheets

(56) References Cited

U.S. PATENT DOCUMENTS

| | | | |
|---|---|---|---|
| 5,184,620 A * | 2/1993 | Cudahy | A61B 5/04085 600/382 |
| 5,660,892 A | 8/1997 | Robbins et al. | |
| 5,788,633 A | 8/1998 | Mahoney | |
| 5,865,740 A | 2/1999 | Kelly et al. | |
| 5,865,741 A | 2/1999 | Kelly et al. | |
| 5,868,671 A | 2/1999 | Mahoney | |
| 5,916,159 A | 6/1999 | Kelly et al. | |
| 6,006,125 A | 12/1999 | Kelly et al. | |
| 6,157,851 A | 12/2000 | Kelly et al. | |
| 6,219,569 B1 | 4/2001 | Kelly et al. | |
| 6,298,255 B1 | 10/2001 | Cordero et al. | |
| 6,473,343 B2 | 10/2002 | Ohba et al. | |
| 6,553,246 B1 | 4/2003 | Wenger | |
| 6,623,312 B2 | 9/2003 | Merry et al. | |
| 6,751,493 B2 | 6/2004 | Wenger | |
| 6,973,343 B2 | 12/2005 | Wenger | |
| 7,299,084 B1 * | 11/2007 | Price | A61B 5/04085 600/372 |
| 7,933,642 B2 * | 4/2011 | Istvan | A61B 5/0006 600/509 |
| 8,238,996 B2 * | 8/2012 | Burnes | A61B 5/04085 600/382 |
| 8,626,260 B2 * | 1/2014 | Crosby | A61B 5/04085 600/391 |
| 2004/0010303 A1 | 1/2004 | Bolea et al. | |
| 2006/0069320 A1 | 3/2006 | Wolff et al. | |
| 2006/0167353 A1 | 7/2006 | Nazeri | |
| 2008/0082959 A1 | 4/2008 | Fowler | |
| 2008/0139894 A1 | 6/2008 | Szydlo-Moore et al. | |
| 2008/0154110 A1 | 6/2008 | Burnes et al. | |
| 2015/0025354 A1 * | 1/2015 | Salonius | A61B 5/6805 600/389 |

\* cited by examiner

MULTIELECTRODE ECG SENSOR

CROSS-REFERENCE TO RELATED APPLICATIONS

This application is a national stage filing under 35 U.S.C. § 371 of International PCT Application No. PCT/US2015/046279, entitled MULTIELECTRODE ECG SENSOR, filed Aug. 21, 2015, which claims the benefit under 35 U.S.C. § 119(e) to U.S. provisional application Ser. No. 62/040,766, entitled MULTIELECTRODE ECG SENSOR, filed Aug. 22, 2014, the disclosure of each of which is incorporated by reference herein in its entirety.

NAMES OF PARTIES TO A JOINT RESEARCH AGREEMENT

This invention was made pursuant to a joint research agreement between the parties Children's Medical Center Corporation and Theranova, LLC.

FIELD

The disclosed embodiments are generally directed to sensors for conducting electrocardiograph measurements, and more particularly to structures suitable for swift and proper placement of electrodes on a patient.

BACKGROUND

Electrocardiographs (hereinafter referred to as "ECGs") are used to provide information about a patient's heart. As is known, the heart generates electrical signals that travel to a patient's skin. Sensors in the form of electrodes are placed on the skin to detect the heart's electrical signals and transmit information to a monitor. The monitor can interpret the signals and produce the ECG. Proper placement of the electrodes on the skin is important to providing a quality ECG.

SUMMARY

In one embodiment, a multielectrode sensor for use in obtaining electrocardiograph measurements of a patient is disclosed. The multielectrode sensor includes a substrate, at least a portion of the substrate being stretchable, and a plurality of electrodes coupled to the substrate. The distance between at least two of the electrodes may be adjustable by stretching the substrate between the at least two electrodes.

In another embodiment, a method of positioning a multielectrode sensor on a patient is disclosed. The multielectrode sensor includes a stretchable substrate and a plurality of electrodes coupled to the substrate. The method includes positioning a first electrode on the patient's torso, stretching the substrate between the first electrode and a second electrode, and positioning a second electrode on the patient's torso.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2b is a cross-sectional view of the multielectrode sensor of FIG. 2a;

DETAILED DESCRIPTION

ECGs use electrodes that are attached to various locations of a patient's torso and limbs to measure and analyze cardiac behavior. Twelve-lead ECGs, which afford the most accurate results, utilize ten electrodes, six of which are positioned on the patient's torso ($V_1$, $V_2$, $V_3$, $V_4$, $V_5$ and $V_6$). Proper placement of electrodes on the patient's torso is essential to a quality ECG as improper electrode placement may result in an inaccurate ECG interpretation. Traditionally, each electrode is individually attached to the patient's torso, which is helpful for different sized patients; however, the individual electrodes can be easily mis-positioned. To assist with proper electrode placement, various structures have been developed, some of which allow an array of electrodes to be attached to the patient's torso. One example includes a strip with slots at desired anatomical locations acting as guides for individual electrode placement. Another example is a strip or such film that includes several of the same electrodes on the film (e.g., three $V_6$ electrodes on the film) to allow a clinician to use the film for different sized patients. It should be appreciated that a clinician may be a doctor, a nurse, a technician, a medical assistant or other medical professional responsible for placing monitoring devices, such as electrodes, on a patient.

According to one aspect, a multielectrode sensor for use with an ECG is disclosed. The multielectrode sensor allows for attachment of a plurality of electrodes to the torso of the patient, which facilitates swift and proper placement of the electrodes. The multielectrode sensor is also designed to have intrinsic configurability between at least some of the individual electrodes, which allows the same sensor to accommodate patients of different sizes (e.g., one-size-fits-all) and also allows a clinician to tailor the sensor to a particular patient. For example, a sensor designed for babies may be manipulated, as will be described, to accommodate babies weighing between about 0.5 kg and 10 kg, and also allows the clinician to place the electrodes in the proper location on each, differently sized baby. Similar one-size-fits-all sensors also may be designed for children and for adults.

Figure 1:
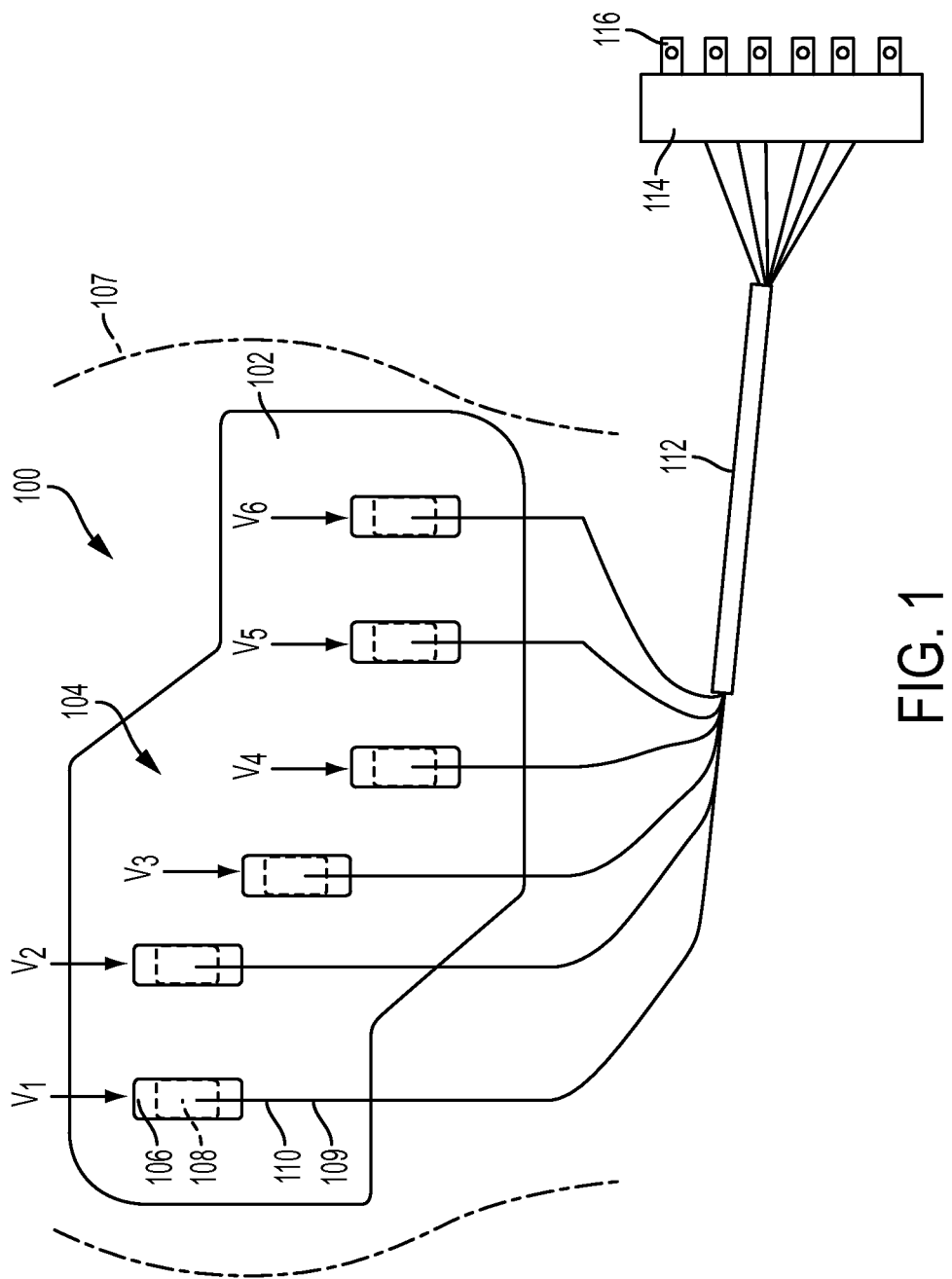
FIG. 1 is a schematic view of a multielectrode sensor according to one embodiment.
Figure 4:
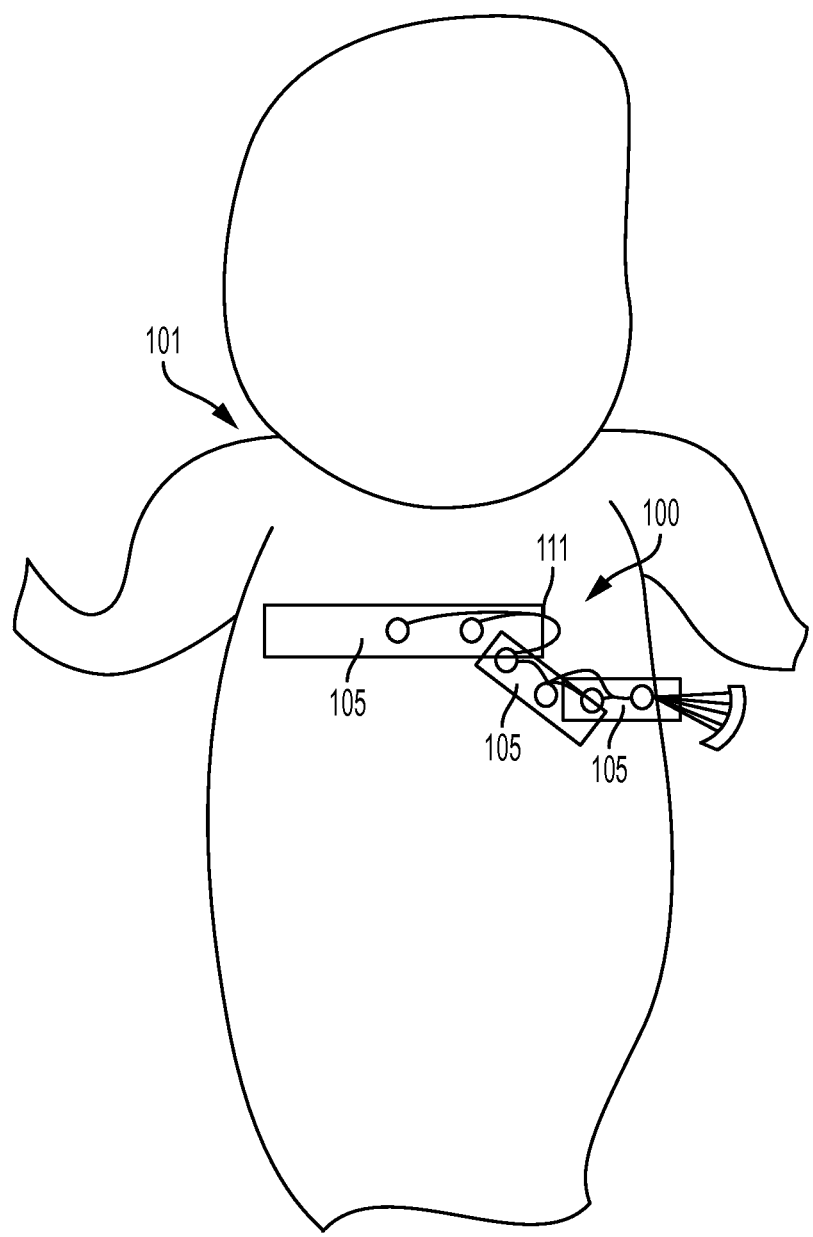
FIG. 4 is a multielectrode sensor according to another embodiment.

The configurability between the individual electrodes is established by changing the spacing between the electrodes. In one embodiment, the sensor electrodes are tethered to each other by a stretchable material or otherwise coupled to a stretchable material. As such, as used herein, "substrate" simply refers to the component to which the electrodes are coupled. Accordingly, the configurability is accomplished by stretching the substrate between the electrodes to move one electrode further away from another, adjacent electrode. In some embodiments, the electrodes are moved horizontally with respect to one another (e.g., to the left and right) when the device is stretched. The electrodes may also be moved vertically with respect to one another (e.g., up and down). In some embodiments, as shown in FIGS. 1 and 2, the multielectrode sensor 100 includes a single substrate 102 with a plurality of electrodes. As is shown in these figures, the multielectrode sensor 100 includes a substrate 102 having six electrodes, although the substrate 102 may have more or fewer electrodes in other embodiments. The multielectrode sensor 100 also may include more than one substrate portion, with each substrate portion having a plurality of electrodes. For example, as shown in FIG. 4, the multielectrode sensor 100 includes three substrate portions 105, each portion having two electrodes. In embodiments having multiple substrate portions 105, the substrate portions 105 may be connected to one another or, as shown in FIG. 4, the substrate portions may be disconnected, with only the electrodes being connected to one another via a wire 111.

As shown in FIGS. 1 and 2, in one embodiment, the multielectrode sensor 100 includes a substrate 102 with a plurality of electrodes, which, in some embodiments, are arranged as an array 104 of electrodes $V_1$, $V_2$, $V_3$, $V_4$, $V_5$ and $V_6$. In some embodiments, the substrate is a flexible or stretchable piece of material. The substrate 102 may be a single piece structure, a multi-piece structure, one or more pieces of mesh, one or more tethers, or a combination thereof, as aspects of the present invention are not limited in this regard. As illustrated in these figures, the substrate 102 is a single-piece component and may have a shape as shown, such as having a dog-leg bend as shown, although other suitably shaped substrates 102 may be used. For example, in some embodiments, the substrate 102 may have a rectangular, square, circular, triangular, other polygonal or other shape. In one embodiment, the substrate may be configured as a strip.

Figure 2A:
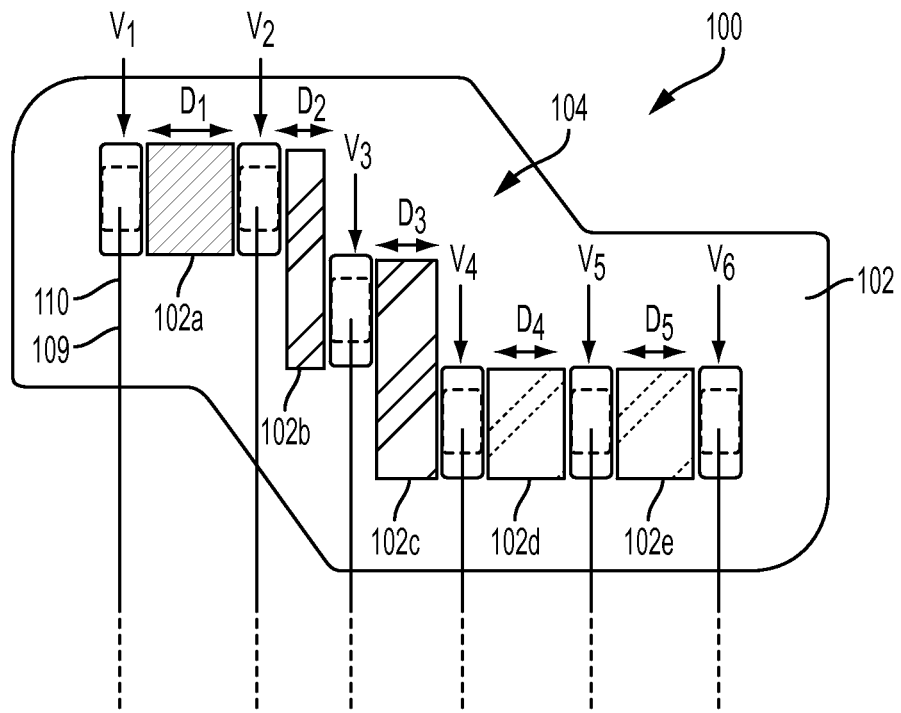
FIG. 2a is a schematic view of the multielectrode sensor of FIG. 1.

As shown in FIGS. 1 and 2, the multielectrode sensor 100 has six electrodes in an array 104. As is shown, the initial location of each electrode $V_1$, $V_2$, $V_3$, $V_4$, $V_5$ and $V_6$ relative to each other on the substrate is pre-defined, yet the in-use position may be changed to allow for proper placement of the electrodes when the multielectrode sensor is positioned on the patient's torso 107, as will be described. As is known, for a proper ECG, the $V_1$ electrode is placed on the patient's torso in the fourth intercostal space, between the fourth and fifth ribs, just to the right of the sternum. The $V_2$ electrode is placed in the fourth intercostal space, just to the left of the sternum. In some embodiments, as shown in FIG. 2a, the $V_1$ and $V_2$ electrodes are horizontally aligned on the substrate 102 and separated by a distance $D_1$. Also for a proper ECG, the $V_3$ electrode is placed on the patient's torso, between electrodes $V_2$ and $V_4$. The $V_4$ electrode is placed on the patient's torso in the fifth intercostal space, between the fifth and sixth ribs, in the mid-clavicular line, the mid-clavicular line being an imaginary line extending down from the midpoint of the clavicle. Electrode $V_5$ is aligned horizontally with electrode $V_4$ and is placed on the patient's torso at the anterior axillary line, the anterior axillary line being an imaginary line extending down from a point midway between the middle of the clavicle and a lateral end of the clavicle, the end closest to the arm. The $V_6$ electrode is aligned horizontally with the $V_4$ and $V_5$ electrodes and is placed on the patient's torso at the midaxillary line, the midaxillary line is an imaginary line extending down from a middle of the patient's armpit. In some embodiment, as shown in FIG. 2a, the $V_4$, $V_5$ and $V_6$ electrodes are horizontally aligned on the substrate 102 with each pair being separated by a distance $D_4$, $D_5$. In some embodiments, the $V_3$ electrode is positioned between the $V_2$ and $V_4$ electrodes, with the $V_3$ electrode being separated from the $V_2$ and $V_4$ electrodes by a distance $D_2$, $D_3$.

FIG. 2a illustrates the multielectrode sensor 100 in an initial, unused state (e.g., the multielectrode sensor 100 before stretching and placement on the patient's torso). As shown in this figure, and as previous described, each electrodes is separated from another, adjacent electrode by a distance. The distance between electrodes $V_1$ and $V_2$ is labeled $D_1$, the distance between electrodes $V_2$ and $V_3$ is labeled $D_2$, the distance between electrodes $V_3$ and $V_4$ is labeled $D_3$, the distance between electrodes $V_4$ and $V_5$ is labeled $D_4$, and the distance between electrodes $V_5$ and $V_6$ is labeled $D_5$.

In some embodiments, the stretchability of the substrate 102 allows the distance $D_1$, $D_2$, $D_3$, $D_4$, $D_5$ between each pair of electrodes $V_1$, $V_2$, $V_3$, $V_4$, $V_5$, $V_6$ to be changed such that the electrodes may be placed on the proper location on the patient's torso. In some embodiments, the distance $D_1$, $D_2$, $D_3$, $D_4$, $D_5$ between each pair of electrodes $V_1$, $V_2$, $V_3$, $V_4$, $V_5$, $V_6$ is increased to allow for proper electrode placement.

Figure 3:
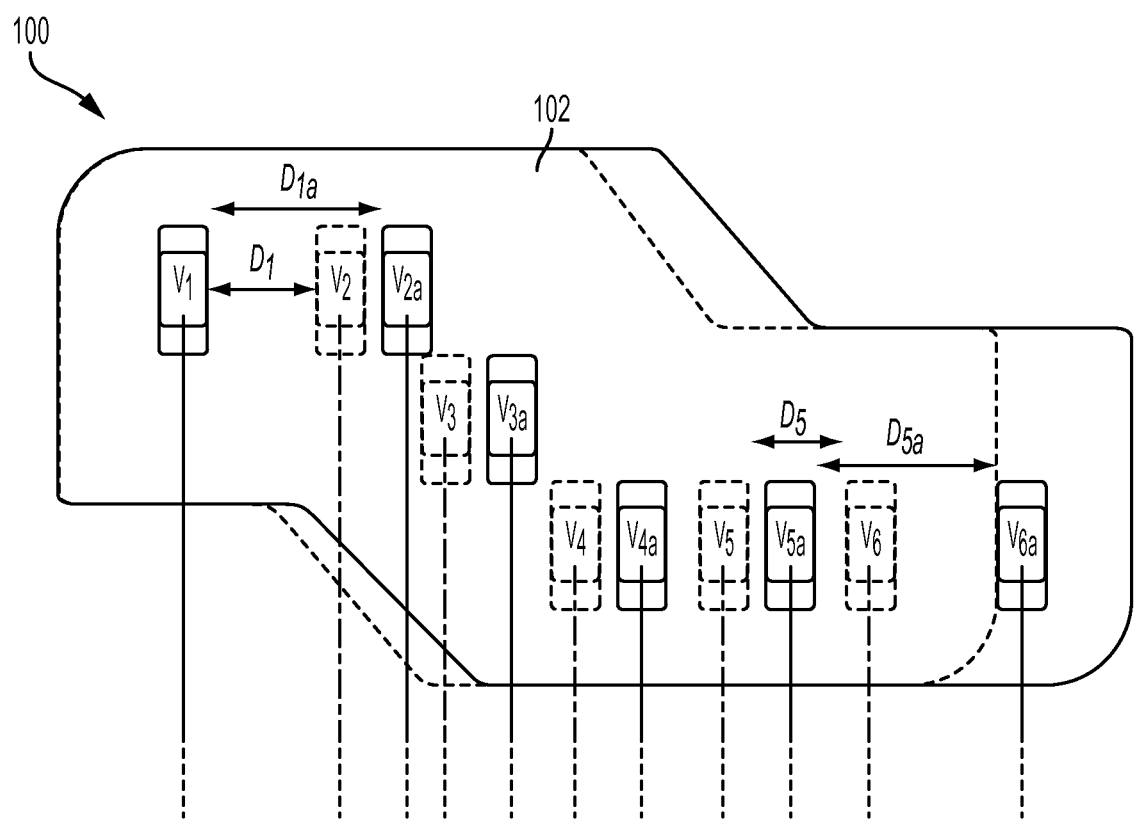
FIG. 3 is a schematic view of the multielectrode sensor of FIG. 1 stretched to an in-use state.

FIG. 3 illustrates an example of the multielectrode sensor 100 in an in-use state (e.g., the multielectrode sensor after stretching and placement on the patient's torso). The dashed lines represent the unstretched state whereas the solid lines represent the stretched state. As shown in this figure, the substrate 102 has been stretched to increase the distance between the $V_1$ and $V_2$ electrodes from $D_1$, in the initial, unused state, to $D_{1a}$, in the in-use state. This also moves the $V_2$ electrode to the in-use position of $V_{2a}$. Stretching the substrate 102 also moves the $V_3$ and $V_4$ electrodes to their in-use positions $V_{3a}$, $V_{4a}$, respectively. FIG. 3 also illustrates stretching the substrate 102 to increase the distance between the $V_5$ and $V_6$ electrodes to $D_{5a}$, which moves the $V_6$ electrode to the in-use position of $V_{6a}$.

Figure 2B:
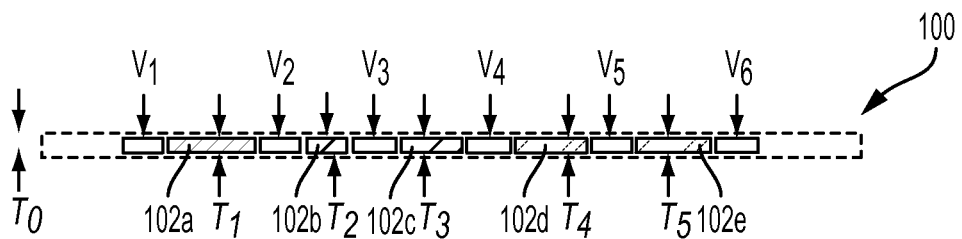

In some embodiments, the stretchability of the substrate 102 between each pair of electrodes $V_1$, $V_2$, $V_3$, $V_4$, $V_5$, $V_6$ is achieved by varying the type and/or composition of the substrate 102. In one embodiment, the stretchability is achieved and also adjusted or tuned by varying the thickness and/or width of the substrate 102 between each pair of electrodes $V_1$, $V_2$, $V_3$, $V_4$, $V_5$, $V_6$. In one embodiment, as shown in FIG. 2b, the thickness of the substrate 102a between electrodes $V_1$ and $V_2$ is labeled $T_1$, the thickness of substrate 102b between electrodes $V_2$ and $V_3$ is labeled $T_2$, the thickness of the substrate 102c between electrodes $V_3$ and $V_4$ is labeled $T_3$, the thickness of the substrate 102d between electrodes $V_4$ and $V_5$ is labeled $T_4$, and the thickness of the substrate 102e between electrodes $V_5$ and $V_6$ is labeled $T_5$. The thickness of the multielectrode sensor 100 is labeled $T_0$.

As shown in FIGS. 2a and 2b, the stretchability between each pair of electrodes may be the same in some embodiments, while in other embodiments, the stretchability may be different between each pair of electrodes. For example, the thickness of the substrate 102 between each pair of electrodes may be the same or it may be different. In another example, the width of the substrate 102 between each pair of electrodes may be the same or it may be different. In yet another example, the material of the substrate 102 between each pair of electrodes may be the same or it may be different. In one embodiment, as shown in FIGS. 2a and 2b, the substrate 102a between the $V_1$ and $V_2$ electrodes is thinner than the substrate 102b, 102c, 102d, 102e between all of the other pairs of electrodes (e.g., $T_1$ is less than $T_2$, $T_3$, $T_4$ and $T_5$). In such an embodiment, the multielectrode sensor 100 provides the greatest stretchability between the $V_1$ and $V_2$ electrodes than between any of the other pairs of electrodes.

In some embodiments, the substrate 102d between the $V_4$ and $V_5$ electrodes and the substrate 102e between the $V_5$ and $V_6$ electrodes also may be stretchable, and, in some embodiments, the stretchability between the $V_4$ and $V_5$ electrodes may be substantially the same as the stretchability between the $V_5$ and $V_6$ electrodes. For example, in some embodiments, the thickness $T_4$ of the substrate 102d between the $V_4$ and $V_5$ electrodes is substantially the same as the thickness $T_5$ of the substrate 102e between the $V_5$ and $V_6$ electrodes. The stretchability of the substrate 102d, 102e between the $V_4$ and $V_5$ electrodes and the $V_5$ and $V_6$ electrodes also may be substantially the same as the stretchability of the substrate 102a between the $V_1$ and $V_2$ electrodes, although the substrate 102d between the $V_4$ and $V_5$ electrodes and the substrate 102e between $V_5$ and $V_6$ are shown as having less stretchability than the substrate 102a between the $V_1$ and $V_2$ electrodes. The stretchability between the $V_4$ and $V_5$ electrodes and between the $V_5$ and $V_6$ electrodes also may differ in other embodiment.

Figure 6A:
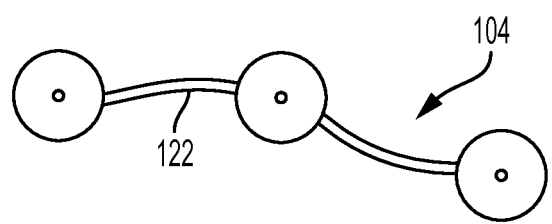
FIG. 6a is multielectrode sensor having an array of electrodes according to one embodiment.
Figure 6B:
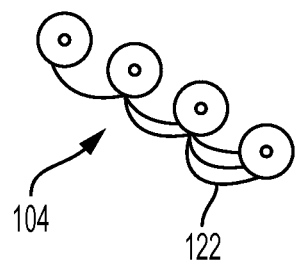
FIG. 6b is a multielectrode sensor having an array of electrodes according to another embodiment.

In some embodiments, the entire substrate 102 is stretchable. In such an embodiment, the portions of the substrate between the electrodes are adjusted or tuned (e.g., the thickness is varied or the material is changed) to achieve the desired stretchability in those portions. In other embodiments, only the portions of the substrate between the electrodes have stretchability, that is, all other portions of the substrate are unstretchable. In some embodiments, as discussed above, and as shown in FIGS. 6a and 6b, the electrodes are connected or tethered to one another via a stretchable material. For example, in one embodiment, the array 104 of electrodes are connected, with the distance between the electrodes being maintained in the unused state, by a bridge 122. Although three and four electrodes are shown as being connected to one another via the bridges 122 in FIGS. 6a and 6b, respectively, more or fewer electrodes may be connected together in other embodiments.

In some embodiments, little to no stretchability is provided between some of the pairs of electrodes. For example, in some embodiments, the substrate 102 between the pair of electrodes is configured such that the electrodes cannot move with respect to one another. As shown in FIGS. 2a and 2b, in one embodiment, the multielectrode sensor 100 is designed such that the distance $D_2$ between the $V_2$ and $V_3$ electrodes and the distance $D_3$ between the $V_3$ and $V_4$ electrodes remains substantially the same in the initial, unused state and in the final, in-use state of the multielectrode sensor 100. In such an embodiment, the thickness $T_2$, $T_3$ of the substrate between the $V_2$ and $V_3$ electrodes and between the $V_3$ and $V_4$ electrodes, respectively, may be greater than the thicknesses of the substrate between any of the of the other pairs of electrodes having stretchability. In some embodiments, the thickness $T_2$, $T_3$ of the substrate between the $V_2$ and $V_3$ electrodes and between the $V_3$ and $V_4$ electrodes, respectively, may be substantially the same as the thickness $T_0$ of the multielectrode sensor 100. Although shown as having little-to-no stretchability in this figure, the multielectrode sensor 100 also may be configured to allow configurability between the $V_2$ and $V_3$ electrodes and between the $V_3$ and $V_4$ electrodes.

In some embodiments, the position of each electrode $V_1$, $V_2$, $V_3$, $V_4$, $V_5$, $V_6$ in the initial, unused state of the multielectrode sensor 100 also corresponds to the final, in-use position of the multielectrode sensor 100. In other words, no adjustment or stretching of the substrate 102 between the electrodes $V_1$, $V_2$, $V_3$, $V_4$, $V_5$, $V_6$ is necessary, and the clinician need only place the multielectrode sensor 100 on the patient's torso, aligning the electrodes in the proper position, and attaching the multielectrode sensor 100 and electrodes to the patient's torso.

In other embodiments, the multielectrode sensor 100 must be adjusted and stretched to fit the patient and ensure that the electrodes are attached at the proper locations. For example, the distance between at least two of the electrodes may be adjusted to allow for proper placement of the electrodes. In such an embodiment, the clinician places the multielectrode sensor 100 on the patient's torso such that the first electrode $V_1$ is positioned and thereafter attached at the fourth intercostal space, to the right of the patient's sternum. If necessary, the clinician may then pull on the multielectrode sensor 100 to stretch the substrate 102a between the $V_1$ and $V_2$ electrodes (increasing $D_1$ to $D_{1a}$, as shown FIG. 3) until the $V_2$ electrode is positioned over and attached to the patient's torso at the fourth intercostal space, to the left of the patient's sternum. The clinician can repeat this step, as necessary, to stretch the substrate 102 between the remaining pairs of electrodes such that the $V_3$, $V_4$, $V_5$, and $V_6$ electrodes are properly placed and thereafter attached to the patient's torso. As previously described, the distance between each of the remaining pairs of electrodes need not be adjusted, that is, the remaining electrodes may simple be placed on the patient's torso without adjusting the distances $D_3$, $D_4$, $D_5$ between the remaining pairs of electrodes. In other embodiments, the multielectrode sensor 100 may be pulled to stretch the substrate 102d, 102e and adjust the distances $D_4$, $D_5$ between the $V_4$ and $V_5$ electrodes and between the $V_5$ and $V_6$ electrodes, respectively, to properly place and attach the $V_4$, $V_5$ and $V_6$ electrodes on the patient's torso.

It should be appreciated that although the above embodiment is shown and described as stretching the substrate relative to the $V_1$ electrode, those of skill in the art will appreciate that the present invention is not so limited and the other electrodes or locations of the substrate may act as the datum point.

In some embodiments, the substrate is formed of a silicone-based material. In such embodiments, the stretchability may be achieved by varying the thickness of the silicone between the electrodes, as described. The stretchability also may be achieved by varying the properties of the silicone between the electrodes (e.g., by varying the durometer value of the silicone between the electrodes as compared to the durometer value of the silicone in other portions of the substrate). In embodiments having a mesh substrate, the stretchability may be achieved by varying the weave of the mesh between the electrodes. For example, to increase the stretchability between the electrodes, as described, the density of the weave of the mesh in between the electrodes may be decreased.

In some embodiments, the combined weight of the electrodes and standard cross-platform connectors (e.g., alligator clips) is substantial enough such that the electrodes may be pulled off of the patient's skin. According to another embodiment, the multielectrode sensor 100 is configured to minimize the weight of the sensor 100 on patient's torso 107 during ECG monitoring. In some embodiments, the weight is reduce by connecting the multielectrode sensor 110 to an ECG machine (not shown) off of the patient's torso. In some embodiments, the weight of the lead is not more than twice the weight of the electrode.

As shown in FIG. 1, in one embodiment, the electrodes may be embedded in the substrate 102. Further, in one embodiment, the multielectrode sensor 110 includes wires 110 connected to the electrodes, at least a portion 109 of each wire 110 are also embedded in the substrate 102. Although a portion 109 of the wire is shown embedded in the substrate 102 in this figure, in other embodiments, the wire 110 also may be separate from the substrate 102. In some embodiments, a length of the wire 110 extending from each electrodes is sufficiently long enough so that a distal end the wire 110 is connected to the ECG machine (not shown) off of the patient's torso 107. In one embodiment, as is shown, the distal end of each wire 110 is connected to a junction box 114, which has contacts 116 that can be used to connect to the ECG machine (not shown), for example via cross-platform connectors (not shown). In some embodiments, the contacts 116 on the junction box 114 are labeled with the corresponding electrode $V_1$, $V_2$, $V_3$, $V_4$, $V_5$, $V_6$ so that the clinician knows which cross-platform connectors (not shown) to connect to each contact 116. In other embodiments, the distal end of the wires 110 may be connected to the cross-platform connectors (e.g., alligator clips). As shown in FIG. 1, in some embodiments, a sleeve 112 is placed around the wires 110. The sleeve 112 may prevent inadvertent snagging or pulling of the wires 110 and, thus, accidental tugging on the sensor 100 once on the patient's torso.

Figure 5:
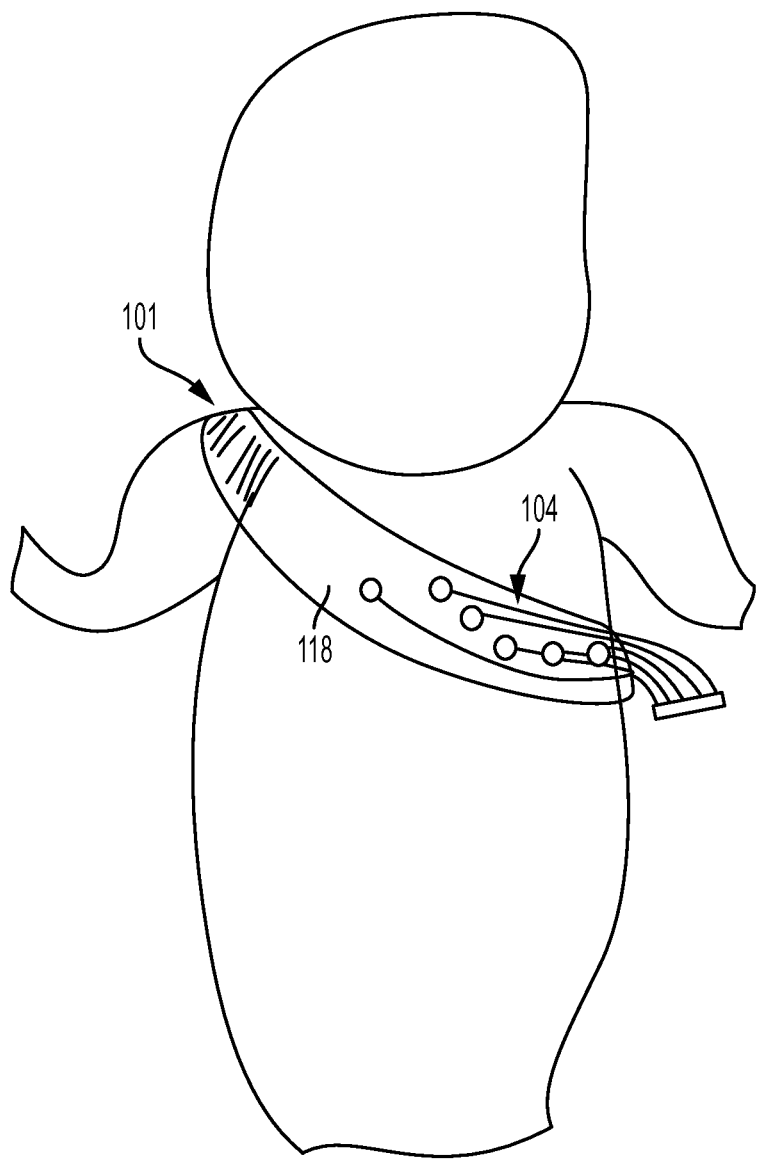
FIG. 5 is a multielectrode sensor according to another embodiment.

In some embodiments, as shown in FIG. 5, the wires 110 connected to each electrode $V_1$, $V_2$, $V_3$, $V_4$, $V_5$, $V_6$ are substantially embedded in the substrate, with only an end portion of the wires extending from one side of the substrate (e.g., the side of the substrate closest to the $V_6$ electrode). In such an embodiment, tangling or snagging of the wires on the babies stomach may be minimized as the wires are only accessible via one side of the substrate.

In some embodiments, as shown in FIG. 1, each electrode comprises a fabric backing 106, a conductive portion 108, and an adhesive (not shown), such as a gel. As previously described, in some embodiments, the wire 110 is connected to each electrode. The electrode may be prepared by layering the conductive portion 108 on top of the adhesive, the wire on top of the conductive portion, and, finally, the fabric backing 106 on top of the conductive portion 108.

In some embodiments, the multielectrode sensor 100 is prepared by placing the electrodes, adhesive side down, on a template, the template providing guides for the desired location of each electrode. The material used to form the substrate is then poured over the template, with the fabric backing 106 serving to facilitate attachment between the substrate 102 and the electrode. Once the substrate 102 has cured, the multielectrode sensor 100, having the embedded array 104 of electrodes, is removed as a single piece.

In some embodiments, the substrate includes a material with a low durometer value (e.g., less than about 30). The durometer value also may be between about 10 and 15. As noted, in one embodiment, the substrate 102 includes a silicone material, which can have a low durometer value to provide the desired stretchability of the substrate 102. The substrate material may be stretched when a stretching force is applied to it and when the force is released, the substrate may return to its original state such that the electrodes are substantially in the same location relative to each other as was the case prior to stretching. In some embodiments, the substrate may lack such a memory such that upon stretching and thereafter removal of the stretching force, the substrate does not contract and the electrodes remain in their stretched position. It should be appreciated that when the substrate is stretched and attached to the skin of the patient, the patient's skin will act to maintain the stretching force on the substrate with little to no contraction of the substrate.

In some embodiments, the multielectrode sensor 100 is configured to allow the sensor to remain on the patient's torso for a desired period of time, that is, the desired period of ECG monitoring, without irritating the patient's skin. For example, in some embodiments, the sensor is configured to remain on the patient's torso for between about 15 minutes and about 1 hour. In other embodiments, the sensor 100 is configured to remain on the patient's torso for up to about 12 hours, 24 hours, or 72 hours, depending upon the length of monitoring. In some embodiments, to allow for attachment of the sensor 100 to the patient's torso, the substrate 102 comprise a material that becomes tacky for adhesion but that does not leave a residue once removed. The substrate also may include a material that allows the sensor to be easily removed and reattached to the patient's torso if the sensor is first, improperly positioned. In some embodiments, a silicone-based material forming the substrate may maintain the sensor 100 on the patient's torso for the desired period of time, as described, while not irritating the patient's skin.

In some embodiments, an adhesive is used to maintain the sensor 100 on the patient's torso for the desired period of time. In some embodiments, a single adhesive layer covers the substrate 102 and all of the electrodes $V_1$, $V_2$, $V_3$, $V_4$, $V_5$, $V_6$ (e.g., a single, patient-contacting adhesive layer). In other embodiments, separate adhesives are placed on each of the electrodes and on the substrate 102. In such an embodiment, different adhesives may be used for the electrodes and the substrate 102 if different levels of attachment are desired. Similar to the substrate, the adhesive may include a material that allows the electrodes and substrate 102 to be easily removed and reattached, if desired. The adhesive also may include a material that is safe and non-irritating for the patient's skin.

In some embodiments, the substrate 102 includes indicators (not shown), either printed on or embedded in the substrate 102. In some embodiments, the indicators acts to alert a clinician to the proper attachment location for each electrode. For example, in one embodiment, the substrate may include an indicator labeled "V1" near the $V_1$ electrode that reminds the clinician that the electrode should be placed in the fourth intercostal space, to the right of the sternum. In another example, the substrate may include an indicator in between the $V_1$ and $V_2$ electrodes that is labeled "Sternum", to remind the clinician that the $V_1$ and $V_2$ electrodes are to be placed to the right and left of the sternum, respectively.

In some embodiments, the multielectrode sensor 100 includes a backing sheet (not shown), which is removably attached to the patient-contacting side of the sensor to protect the substrate 102 and electrodes $V_1$, $V_2$, $V_3$, $V_4$, $V_5$, $V_6$. In some embodiments, a single backing sheet (not shown) may cover the entire multielectrode sensor, while, in other embodiments, multiple backing sheets may be used. For example, in some embodiments, separate backing sheets are removably attached to each of the electrodes $V_1$, $V_2$, $V_3$, $V_4$, $V_5$, $V_6$ and one backing sheet is attached to the substrate 102. In other embodiments, backing sheets cover each of the electrode regions (e.g., a backing sheet covers both the electrode and the surrounding substrate 102 in a particular region, such as the $V_1$ electrode region.) In some embodiments, the backing sheet is removed from the multielectrode sensor 100 and electrodes prior to attaching the multielectrode sensor 100 to the patient's torso.

Although the previous embodiments have shown and described the multielectrode sensor 100 with a substrate 102 having a plurality electrodes, other suitable arrangements may be used to attach the array of electrodes. For example, as shown in FIG. 5 a stretchable harness 118 which may be wrapped around the patient's torso may be used to attach the array of electrodes. As with the previous examples, and as shown in FIG. 5, the electrodes and wires may be embedded in the harness 118, with the connection between the harness 118 and the ECG machine occurring off of the patient's torso.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

The invention claimed is:

1. A multielectrode sensor for use in obtaining electrocardiograph measurements of a patient, the sensor comprising:
 a substrate, at least a portion of the substrate being stretchable; and
 a plurality of electrodes coupled to the substrate, the plurality of electrodes including V1, V2, V3, V4, V5, and V6 electrodes;
 wherein a distance between at least the V1 and V2 electrodes and between the V4 and V5 electrodes is adjustable by stretching the substrate between the V1 and V2 electrodes and between the V4 and V5 electrodes;
 wherein a first thickness of the substrate between the V1 and V2 electrodes is less than or equal to a second thickness of the substrate between the V4 and V5 electrodes such that a first stretchability of the substrate between the V1 and V2 electrodes is greater than or equal to a second stretchability of the substrate between the V4 and V5 electrodes; and
 wherein the first thickness is less than a third thickness of the substrate between the V2 and V3 electrodes such that the first stretchability is greater than a third stretchability of the substrate between the V2 and V3 electrodes.

2. The multielectrode sensor of claim 1, wherein the substrate comprises a silicone material.

3. The multielectrode sensor of claim 1, wherein the V1 electrode is adapted to be positioned on a first side of the patient's sternum and the V2 electrode is adapted to be positioned on a second side of the patient's sternum.

4. The multielectrode sensor of claim 1, wherein a distance between the V5 and V6 electrodes is adjustable by stretching the substrate between the V5 and V6 electrodes.

5. The multielectrode sensor of claim 4, wherein the first thickness is less than or equal to a fourth thickness of the substrate between the V5 and V6 electrodes such that the first stretchability is greater than or equal to a fourth stretchability of the substrate between the V5 and V6 electrodes.

6. The multielectrode sensor of claim 5, wherein the second thickness differs from the fourth thickness.

7. The multielectrode sensor of claim 5, wherein the second thickness is equal to the fourth thickness such that the second stretchability is substantially the same as a fourth stretchability.

8. The multielectrode sensor of claim 5, wherein the first thickness is less than at least one of the second thickness and the fourth thickness.

9. The multielectrode sensor of claim 1, further comprising a backing sheet removably attached to a patient-contacting side of the substrate.

10. The multielectrode sensor of claim 1, wherein each electrode comprises an adhesive on a patient-contacting side of the electrode.

11. The multielectrode sensor of claim 1, wherein each of the electrodes is connected to a wire, the wire being at least partially disposed in the substrate.

12. The multielectrode sensor of claim 11, wherein a distal end of each wire opposite the electrode is adapted to be connected to at least one of an electrocardiograph machine and a connector.

13. The multielectrode sensor of claim 12, wherein each wire is adapted to be connected to at least one of the electrocardiograph machine and the connector off of the patient's torso.

14. The multielectrode sensor of claim 1, wherein the substrate is a tether between adjacent electrodes.

15. The multielectrode sensor of claim 1, wherein the electrodes are attached to a single substrate component.

16. The multielectrode sensor of claim 1, wherein the first thickness is less than a fifth thickness of the substrate between the V3 and V4 electrodes such that the first stretchability is greater than a fifth stretchability of the substrate between the V3 and V4 electrodes.

17. The multielectrode sensor of claim 16, wherein the third thickness is equal to the fifth thickness.

18. The multielectrode sensor of claim 17, wherein a distance between each of the V2 and V3 electrodes and the V3 and V4 electrodes is substantially the same when the substrate is in a stretched position and an unstretched position.

19. A method of positioning a multielectrode sensor on a patient, the method comprising:
 providing a multielectrode sensor comprising:
  a stretchable substrate and a plurality of electrodes coupled to the substrate, the plurality of electrodes including V1, V2, V3, V4, V5, and V6 electrodes;
  wherein a distance between at least the V1 and V2 electrodes and between the V4 and V5 electrodes is adjustable by stretching the substrate between the V1 and V2 electrodes and between the V4 and V5 electrodes;
  wherein, in an unstretched state, a first thickness of the substrate between the V1 and V2 electrodes is less than or equal to a second thickness of the substrate between the V4 and V5 electrodes such that a first stretchability of the substrate between the V1 and V2 electrodes is greater than or equal to a second stretchability of the substrate between the V4 and V5 electrodes; and
  wherein, in the unstretched state, the first thickness is less than a third thickness of the substrate between the V2 and V3 electrodes such that the first stretchability is greater than a third stretchability of the substrate between the V2 and V3 electrodes;
 positioning the V1 electrode on the patient's torso;
 positioning the V2 electrode on the patient's torso;
 positioning the V3 electrode on the patient's torso;
 positioning the V4 electrode on the patient's torso;
 positioning the V5 electrode on the patient's torso; and
 positioning the V6 electrode on the patient's torso.

20. The method of claim 19, further comprising stretching the substrate between at least the V1 and V2 electrodes and between the V4 and V5 electrodes.

21. The method of claim 20, wherein in an unstretched state, the first thickness is less than or equal to a fourth thickness of the substrate between the V5 and V6 electrodes such that the first stretchability is greater than or equal to a fourth stretchability of the substrate between the V5 and V6 electrodes.

22. The method of claim 21, further comprising stretching the substrate between the V5 and V6 electrodes.

23. The method of claim 22, further comprising attaching each of the V1, V2, V3, V4, V5, and V6 electrodes to the patient's torso.

24. The method of claim 21, wherein the first thickness is less than at least one of the second thickness and the fourth thickness.

25. The method of claim 19, wherein the multielectrode sensor comprises a removable backing sheet on a patient-contacting side of the substrate, wherein the method further comprises removing the backing sheet prior to positioning the V1 electrode.

26. The method of claim 19, wherein:
   positioning the V1 electrode comprises positioning the V1 electrode to a first side of the patient's sternum; and
   positioning the V2 electrode comprises positioning the V2 electrode to a second side of the patient's sternum.

* * * * *